US009835501B2

(12) United States Patent
Zheng et al.

(10) Patent No.: US 9,835,501 B2
(45) Date of Patent: Dec. 5, 2017

(54) WIRELESS TEMPERATURE AND HUMIDITY SENSOR AND SYSTEM, AND MEASUREMENT METHOD

(71) Applicant: SH INFOTECH CO., LTD., Shanghai (CN)

(72) Inventors: Qihong Zheng, Shanghai (CN); Zechen Li, Shanghai (CN)

(73) Assignee: SH Infotech Co., Ltd., Shanghai (CN)

( * ) Notice: Subject to any disclaimer, the term of this patent is extended or adjusted under 35 U.S.C. 154(b) by 337 days.

(21) Appl. No.: 14/417,656

(22) PCT Filed: Nov. 12, 2012

(86) PCT No.: PCT/CN2012/084452
§ 371 (c)(1),
(2) Date: Jan. 27, 2015

(87) PCT Pub. No.: WO2014/015577
PCT Pub. Date: Jan. 30, 2014

(65) Prior Publication Data
US 2015/0260587 A1    Sep. 17, 2015

(30) Foreign Application Priority Data

Jul. 27, 2012  (CN) .......................... 2012 1 0264920

(51) Int. Cl.
*G01K 11/26* (2006.01)
*G01N 29/24* (2006.01)
(Continued)

(52) U.S. Cl.
CPC ......... *G01K 11/265* (2013.01); *G01N 29/022* (2013.01); *G01N 29/036* (2013.01);
(Continued)

(58) Field of Classification Search
CPC .................................................... G01K 11/265
See application file for complete search history.

(56) References Cited

U.S. PATENT DOCUMENTS 7,549,791 B2 *  6/2009  Penavaire ................ G01K 7/32
                                                    310/313 R
7,733,220 B2 *  6/2010  Libby ................ G08B 13/2494
                                                    340/511
(Continued)

FOREIGN PATENT DOCUMENTS

CN          101008586        8/2007
CN          101023334        8/2007
(Continued)

OTHER PUBLICATIONS

Li Ping et al., "The Passive Wireless Temperature Sensor of the SAW Resonator," Chinese Journal of Scientific Instrument, Aug. 2003, vol. 24, No. 4, p. 403-405.
(Continued)

*Primary Examiner* — Clayton E Laballe
*Assistant Examiner* — Leon W Rhodes, Jr.
(74) *Attorney, Agent, or Firm* — Hamre, Schumann, Mueller & Larson, P.C.

(57) ABSTRACT

The present invention provides a wireless temperature and humidity sensor and system, and measurement method. The wireless temperature and humidity sensor comprises a substrate, a feeding network, an antenna and surface acoustic wave resonators, wherein the surface acoustic wave resonators are fed by said feeding network through said antenna. Said surface acoustic wave resonator comprises a reference resonator and measuring resonators. The resonant frequency difference between said reference resonator and said measuring resonators is used to modulate the temperature and/or humidity to be measured. Said system can monitor both temperature and humidity simultaneously, or monitor
(Continued)

humidity or temperature selectively. Furthermore, frequency drift caused by aging of the sensor material and the connector is effectively suppressed by the differential modulation, thereby improving long-term stability of measurement and avoiding recalibration.

15 Claims, 3 Drawing Sheets

(51) Int. Cl.
  *G01N 29/02* (2006.01)
  *G01N 29/30* (2006.01)
  *G01N 29/036* (2006.01)
(52) U.S. Cl.
  CPC ..... *G01N 29/2462* (2013.01); *G01N 29/2481* (2013.01); *G01N 29/30* (2013.01); *G01N 2291/02845* (2013.01); *G01N 2291/02881* (2013.01); *G01N 2291/0423* (2013.01)

(56) References Cited

U.S. PATENT DOCUMENTS

| | | | |
|---|---|---|---|
| 8,317,392 | B2 * | 11/2012 | Cobianu ............ H03H 9/02535 310/313 B |
| 8,904,850 | B1 * | 12/2014 | Allendorf ............ G01N 29/022 310/313 B |
| 2007/0046479 | A1 | 3/2007 | Hines |
| 2007/0051176 | A1 | 3/2007 | Liu |
| 2008/0169724 | A1 | 7/2008 | Bhattacharjee et al. |
| 2008/0303378 | A1 | 12/2008 | Lee et al. |
| 2009/0121847 | A1 | 5/2009 | Solie et al. |
| 2009/0267761 | A1 | 10/2009 | Georgescu et al. |
| 2010/0141087 | A1 | 6/2010 | Bostan et al. |
| 2010/0313398 | A1 | 12/2010 | Chommeloux et al. |
| 2012/0036917 | A1 * | 2/2012 | Avramescu .......... G01N 29/022 73/24.04 |
| 2012/0174678 | A1 | 7/2012 | Gallagher et al. |
| 2014/0319964 | A1 * | 10/2014 | Andle ................ H03H 9/02551 310/313 A |

FOREIGN PATENT DOCUMENTS

| | | |
|---|---|---|
| CN | 101251599 | 8/2008 |
| CN | 101348059 | 1/2009 |
| CN | 101458230 | 6/2009 |
| CN | 201348624 | 11/2009 |
| CN | 101644608 | 2/2010 |
| CN | 101650247 | 2/2010 |
| CN | 102042844 | 5/2011 |
| CN | 102297895 | 12/2011 |
| CN | 102313614 | 1/2012 |
| CN | 102350285 | 2/2012 |
| CN | 102353473 | 2/2012 |
| EP | 2418482 | 2/2012 |

OTHER PUBLICATIONS

Li Tianli et al., "A Novel SAW Sensor for Temperature and Pressure Measurement," Nanotechnology and Precision Engineering, Nov. 2009, vol. 7, No. 6, p. 563-568.
Liu Shuang-lin et al., "Wireless temperature sensing system using a passive SAW resonator," Journal of Transducer Technology, Apr. 2002, vol. 21, No. 4, p. 22-24.
International Search Report for application No. PCT/CN2012/084452, dated Apr. 18, 2013, 8 pages.
Supplementary European search report for European patent appl. No. 12881689.9, dated Apr. 26, 2016 (9 pages).

* cited by examiner

WIRELESS TEMPERATURE AND HUMIDITY SENSOR AND SYSTEM, AND MEASUREMENT METHOD

FIELD

The present invention relates to a wireless sensor, in particular to a temperature and humidity sensor using surface acoustic wave resonators.

BACKGROUND

Surface Acoustic Wave (SAW) sensor is a kind of sensor in which the SAW acts as an environment dependent information carrier. This kind of sensor has properties of high precision, fast response, small size, etc., and is widely applied in fields of aerospace, food hygiene, environmental monitoring, pharmaceutical chemicals, process monitoring, military security, etc., in which SAW sensor displays its unique technical advantages.

Currently, a variety of SAW multi-parameter sensors have been disclosed. For example, Chinese Utility Model CN201837405U disclosed a backscattering surface acoustic wave sensor with pulsed excitation, wherein wireless pulse signals emitted by a remote sensing device are received by a sensor antenna and drives an interdigital transducer to generate radio frequency surface acoustic wave. The acoustic wave pulse is reflected by a reflector and reversely reflected to the remote sensing device by the connected antenna. Temperature and other sensitive variations are extracted during detection of changes in reflection i.e. the delay in the sensor. Chinese patent application CN102313614 disclosed a surface acoustic wave thermometer with improved accuracy, wherein a plurality of transmitters are used to generate backscattering pulse sequences with time intervals, and the temperature detection accuracy is improved by combining time delay differences among those sequences of pulses and phase differences of a plurality of pulses at a single frequency. The patents described above employ a SAW device comprising piezoelectric materials. It should be noted that a drift will appear in backscattering time delay with the aging of piezoelectric materials or electrical connectors, which affects the long-term stability of the measurement. Meanwhile, the structure comprises delay line of larger size, and thus is uneasy to be miniaturized. Also, reliable wireless communication distance is reduced since such high path loss has been introduced.

In addition, China Patent CN201348624Y further disclosed a multi-channel surface acoustic wave chemical sensor, wherein such sensor comprises a plurality of parallel surface acoustic wave detecting channels and a reference channel. Frequency difference between detecting channels and the reference channel is generated by a frequency mixer and delivered to an analyzing device via cables. The invention needs to deliver frequency domain differential signals at low frequency via cable connection, and contains an active peripheral circuit, making it impossible to obtain a passive wireless sensor. Further, the sensor does not include function(s) of temperature or humidity measurement.

SUMMARY

The objective of the present invention is to provide a miniaturized wireless temperature and humidity sensor which maintains measurement accuracy against the aging of the devices.

According to the first aspect of the present invention, it provides a wireless temperature and humidity sensor, comprising a substrate, a feeding network, an antenna and surface acoustic wave resonators, wherein said surface acoustic wave resonators are fed by said feeding network through said antenna;

said surface acoustic wave resonators comprise a reference resonator and measuring resonators; and the resonant frequency difference between said reference resonator and said measuring resonators is used to modulate the temperature and/or humidity to be measured.

In a preferred embodiment, in said wireless temperature and humidity sensor, said measuring resonator comprises a humidity measuring resonator and a temperature measuring resonator, wherein said reference resonator, said humidity measuring resonator and said temperature measuring resonator are connected in parallel;

said temperature measuring resonator has different frequency-temperature coefficients from those of said reference resonator; a hydrophilic coating is applied on the surface of said humidity measuring resonator such that said humidity measuring resonator has different frequency-humidity coefficients from those of said reference resonator. In a preferred embodiment, said temperature measuring resonator is placed in a closed packaging structure, so as to monitor temperature selectively.

In a preferred embodiment, said humidity resonator is packaged by a hydrophilic thin-film coating, so as to selectively monitor humidity.

In a preferred embodiment, said sensor is able to monitor both temperature and humidity simultaneously, or to monitor temperature or humidity selectively.

In a preferred embodiment, said reference resonator and said measuring resonator are made on single or separate pieces of piezoelectric substrates with single layer or stratified layers.

In a preferred embodiment, said reference resonator and said measuring resonator have different rotation angles relative to the substrate's crystal orientation.

In a preferred embodiment, said film coating is applied on the surface of said substrate and said humidity measuring resonator by vapor or liquid phase deposition.

According to the second aspect of the present invention, it provides a wireless temperature and humidity sensor system, comprising a substrate, a feeding network, an antenna, surface acoustic wave resonators and a remote sensing device, wherein said surface acoustic wave resonators are fed by said feeding network through said antenna;

said surface acoustic wave resonators comprise a reference resonator and a measuring resonator, wherein said reference resonator and said measuring resonator have different rotation angles relative to the substrate's crystal orientation;

the resonant frequency difference between said reference resonator and said measuring resonator is used to modulate temperature and/or humidity to be measured; and said remote sensing device scans the resonant frequency or the phase of the backscattering signal from said surface acoustic wave resonators and calculates the difference values therebetween, so as to extract temperature or humidity to be measured.

In a preferred embodiment, said temperature and humidity sensor operates at a frequency range different from that of adjacent sensors of same type, so as to facilitate simultaneously query by said remote sensing device.

In a preferred embodiment, said remote sensing device includes a human-machine interface to provide temperature and/or humidity readings, and a processing means to provide an alarm signal of preset threshold.

In a preferred embodiment, said remote sensing device comprises a wired or wireless repeater or hub, so as to achieve cluster and maintain simplex or duplex communications with a remote monitoring device.

According to the third aspect of the present invention, it provides a method for measuring temperature and/or humidity, wherein the wireless temperature and humidity sensor and its system according described above is employed in the method, and the frequency difference between said reference resonator and said measuring resonator is used to modulate temperature and/or humidity.

According to the fourth aspect of the present invention, it provides a method for measuring temperature and/or humidity, comprising the following steps: arranging said wireless temperature and humidity sensor described above on an object to be measured; obtaining frequencies of said reference resonator and said measuring resonator and calculating the frequency difference between said reference resonator and said measuring resonator; and calculating the temperature and/or humidity of the object based on said frequency difference.

In the wireless temperature and humidity sensor according to the first aspect of the present invention, all surface acoustic wave resonators are fed by said feeding network through said antenna. All resonators operate at adjacent or the same resonant frequency, and resonant frequency difference between resonators is used to modulate the temperature and/or humidity to be measured. The reference resonator and each measuring resonator are processed on a same substrate along preferred orientations, achieving different rotation angles relative to the substrate's crystal orientation respectively, thereby said reference resonator has a different frequency-humidity coefficient from that of each humidity measuring resonator. Resonators may be packaged in a same package structure or separate package structures. Meanwhile, a hydrophilic coating is applied on the surface of one of the measuring resonators and contacts with the external environment directly so that the measuring resonator has a different frequency-humidity coefficient from that of the reference resonator. The resonator with the hydrophilic coating provides the measurement of humidity, while the resonator without hydrophilic coating provides the measurement of temperature. Besides, the measurement of temperature can be further used to compensate the temperature influence in humidity measurement. Furthermore, frequency drift or phase drift caused by aging of the resonator material and the connector is effectively suppressed during differential modulation.

In the wireless temperature and humidity sensor system according to the second aspect of the present invention, said sensor cooperates with the remote sensing device. Said remote sensing device employs band-limited frequency modulated continuous electromagnetic wave to illuminate and interrogate said sensor, after the sensor antenna receives the wave, the SAW resonator is motivated and feeds back to the remote sensing device through the antenna. When the measured temperature or humidity is lower or higher than the preset threshold, the device will alarm and deliver an alarm signal to a remote receiver.

DRAWINGS

Figure 3:
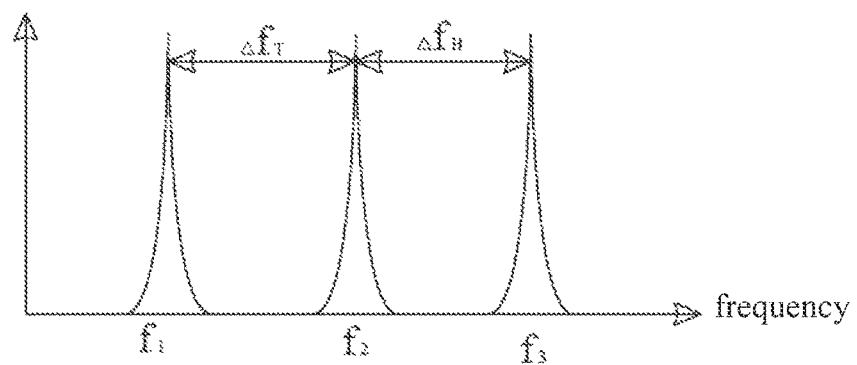
Figure 4:
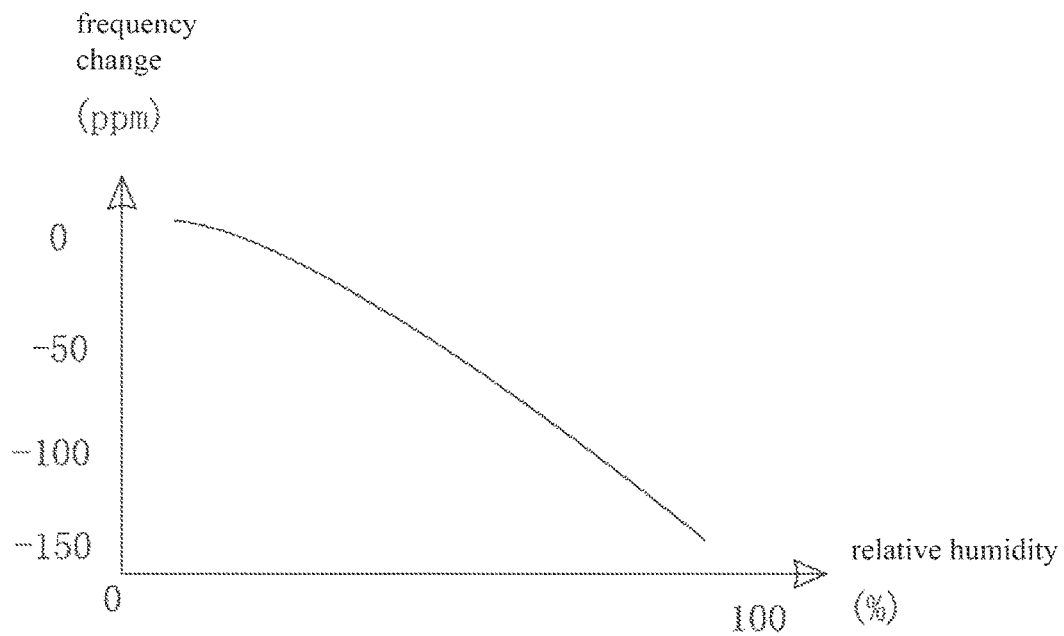
Figure 5:
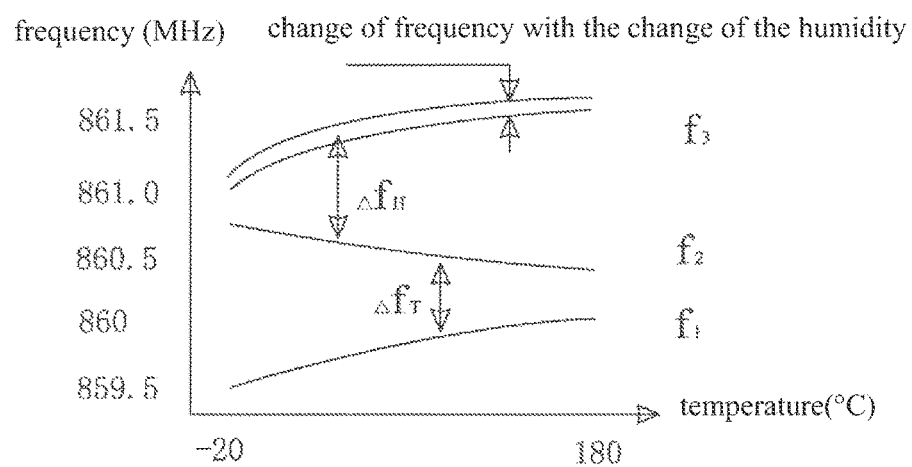

FIG. 3 is a schematic view showing the frequency spectrum and frequency difference according to an embodiment of the sensor of the present invention; and FIGS. 4 and 5 is a graph showing the relationship between humidity, temperature and frequency of an embodiment, wherein FIG. 4 shows the change of frequency with that of relative humidity during humidity measurement and FIG. 5 shows the changes of frequency and frequency difference with that of temperature and humidity.

DETAILED DESCRIPTION

Hereinafter, preferred embodiments of the present invention will be described in detail with reference to the drawings so that the purpose, features and advantages of the present invention will be better understood. It should be understood that the embodiments shown in the drawings are not to limit the scope of the invention, but merely to illustrate the true spirit of the technical solution of the present invention.

Figure 1:
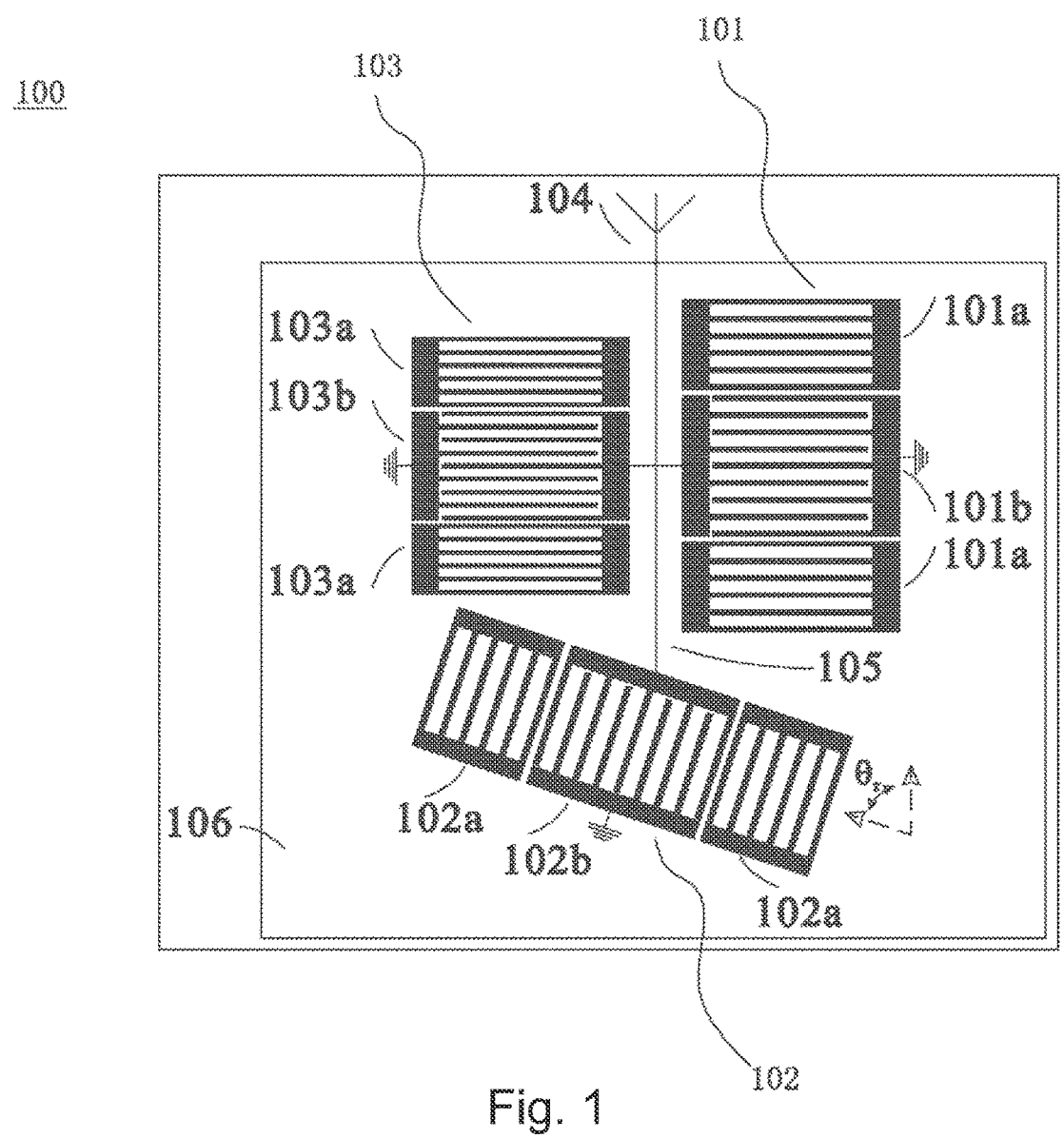
FIG. 1 is a schematically top view of the structure of a wireless passive temperature and humidity sensor according to the present invention.

FIG. 1 shows a schematically top view of the structure of a wireless passive temperature and humidity sensor 100 according to the present invention. As shown in FIG. 1, the sensor 100 comprises a piezoelectric substrate 106, an integrated antenna 104, a feeding network 105, a temperature measuring resonator 101, a reference resonator 102, and/or a humidity measuring resonator 103, wherein the temperature measuring resonator 101 and the humidity measuring resonator 103 are measuring resonators. The piezoelectric substrate 106 is a temperature dependent crystal or film. The hardness, density and size of the piezoelectric will be changed with temperature. In the practice, material, slice orientation and thickness of the piezoelectric substrate 106 may be selected according to a specific application. Preferably, the piezoelectric substrate 106 is made of lithium niobate, quartz, zinc oxide, aluminum nitride, cadmium sulfide, or lanthanum gallium silicate or the like. In addition, the bottom of the substrate further comprises a supporting layer. Preferably, the support layer is made of ceramics or metals, and the thickness of the supporting layer can be determined as desired.

The integrated antenna 104 is a miniaturized integrated antenna. In this embodiment, it may be a meander line dipole antenna, a microstrip patch, an inverted-F or a slot antenna. The radio frequency ground of the antenna is connected with the ground of the sensor. Meanwhile, the feed efficiency can be improved via an optional impedance matching network. The integrated antenna is used for delivery or feedback of temperature and/or humidity signal, and also used for the power supply of the humidity measuring resonator, temperature measuring resonator and the reference resonator.

The feeding network 105 is connected to the antenna port, for example, through microstrip lines or bonding wires. The length, diameter or width of microstrip lines or bonding wires can be determined as desired.

The resonators 101, 102 and 103 are surface acoustic wave resonators, which respectively comprise interdigital transducers 101*b*, 102*b* and 103*b*, and respectively comprise short circuit reflectors 101*a*, 102*a* and 103*a*. Interdigital transducers work at the same frequency with corresponding reflectors, and resonators. The resonators operate at resonance frequencies $f_1$, $f_2$ and $f_3$ which are adjacent but not overlapping respectively. Resonators 101, 102 and 103 are connected in parallel, and the reference resonator 101*h* as a different angle $\theta_r$ relative to the substrate's crystal orientation as compared to measuring resonators 102 and 103. Preferably, the angle $\theta_r$ ranges from 25° to 45°.

Figure 2:
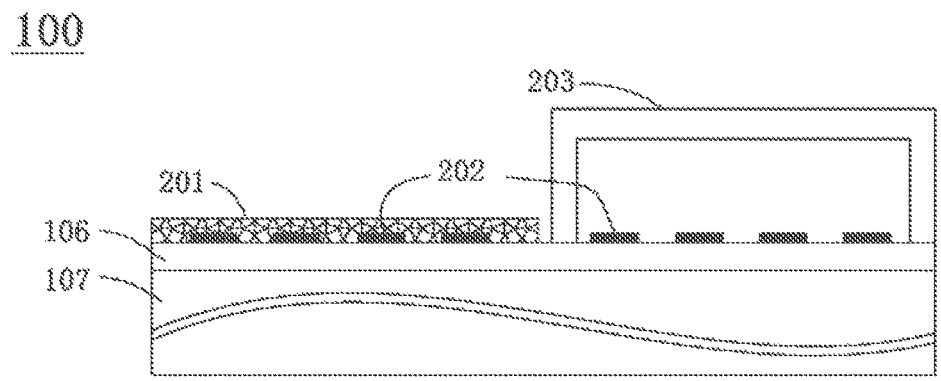
FIG. 2 is a schematically section view of the structure of a wireless temperature and humidity sensor according to the present invention.

FIG. 2 shows a schematically section view of the structure of the wireless passive temperature and humidity sensor 100 according to the present invention, wherein the substrate 107 is a passive substrate acting as a supporter. In this embodiment, the substrate 107 is a metal bracket. The piezoelectric substrate 106 is a temperature dependent piezoelectric crystal which can be formed by fixed the slices prepared by single crystal growth process on the bracket, or the piezoelectric substrate 106 is a piezoelectric film which can be coated on the surface of the bracket via physical or chemical vapor phase film deposition. Then, metal film structures 202 (i.e., the interdigital transducers of the resonators) with specific shape and thickness are processed on the piezoelectric substrate via surface micromachining processes, such as, photolithography, laser engraving, printing or bonding, etc. Said metal film structures may be made of aluminum, gold, tungsten, copper, titanium and its alloys. It should be noted that each of the resonators 101, 102, 103 may be made on a single or a group of piezoelectric substrates with a single layer or stratified layers.

Resonators 101, 102 and 103 may be packaged by two packaging methods, namely by a film coating 201 or a housing 203. Wherein, the film coating 201 may be applied on the surfaces of the piezoelectric substrate and the metal film structure via vapor or liquid phase film deposition. In this embodiment, alumina oxide material (or silicon oxide and other materials) is used to form a passivated surface so that the temperature measuring resonator 101 and the reference resonator 102 are sealed. Alternatively, porous materials with high porosity, such as, zinc oxide or aluminum nitride, are used to form a hydrophilic thin-film coating 201 absorbing vapor in order to package the humidity measuring resonator 103, wherein the upper surface of the hydrophilic thin-film coating 201 is exposed to external environment. In the embodiment shown in the drawings, porous materials with high porosity, such as, zinc oxide or aluminum nitride, are used to form a hydrophilic thin-film coating 201 absorbing vapor to package the humidity measurement resonator 103, while a metal, ceramic or plastic housing is fixed over the temperature measuring resonator 101 and the reference resonator 102 via bonding or welding to package the temperature measuring resonator and the reference resonator.

In another preferred embodiment, an interdigital transducer with aluminum or copper layer, comprising a lithium niobate substrate is used in the sensor 100, wherein thickness of the aluminum or copper layer is 160 nm. A metal bracket is provided at the bottom of the piezoelectric substrate, wherein thickness of the metal bracket may range from 600 micrometers to a few millimeters. Preferably, in this embodiment, the thickness of the metal bracket is 1 mm. Resonators 101, 102, and 103 respectively contains 50 pairs of electrodes and reflection gratings with 100 period length symmetrically distributed at both sides of the resonator 100. The designed operating frequency of the sensor is about 860 MHz. First, the humidity measuring resonator 103 is packaged by porous zinc oxide film, and then the temperature measuring resonator 101 and the reference resonator 102 are inertly packaged by silicon oxide film.

FIG. 3 is a graph showing the frequency spectrum structure and frequency difference according to an embodiment of the sensor 100 of the present invention. In this example, resonators operates at frequencies $f_1$, $f_2$ and $f_3$ respectively, wherein the temperature measurement resonator works at frequency $f_1$, the reference resonator works at frequency $f_2$, and the humidity measurement resonator works at frequency $f_3$. Frequency difference $\Delta f_T$ is used for modulating the temperature and frequency difference $\Delta f_H$ is used for modulating humidity.

$$\Delta f_T = f_2 - f_1 \tag{1}$$

$$\Delta f_H = f_3 - f_2 \tag{2}$$

It should be noted that when there are sensors of same type nearby, preferred frequency range is required to avoid frequency conflicts and ensure that the remote sensing device can simultaneously query (i.e. detect and identify) these sensors.

FIGS. 4 and 5 is a graph showing the relationship between humidity, temperature and frequency of an embodiment, wherein FIG. 4 shows the change of frequency with that of relative humidity during humidity measurement and FIG. 5 shows the change of frequency and frequency difference with that of temperature and humidity.

Specifically, the coating (film) on the upper surface of the humidity measuring resonator changes its density $\rho$ with outside environment vapor partial pressure $C_V$ according to the following rule:

$$\rho(C_V) = \rho_0 + \frac{C_V}{k + \frac{C_V}{\rho_v}} \tag{3}$$

Wherein, k is a constant determined by film thickness, $\rho_v$ is vapor density. Moreover, the thickness of the film becomes thicker with the adsorption of steam.

FIG. 5 shows that these two changes cause the change of high-frequency sound waves velocity of the humidity measuring resonator coated with the film, thereby causes the frequency change. When relative humidity changes within the range of 0% to 100%, frequency change can reach 150 ppm. It should be noted that, at this time, frequency difference $\Delta f_H$ for modulating humidity is a total frequency difference including frequency changes caused by possible temperature change $\Delta T = T - T_0$ with respect to room temperature and humidity change $\Delta H = H - H_0$ with respect to reference ambient humidity (wherein $T_0$ is room temperature, $H_0$ is reference ambient humidity), the relative humidity is obtained in the following manner:

$$\Delta H - H_C = \sqrt{\Sigma_{i=0}^M \beta_i (\Delta f_H)^i + \Sigma_{i=0}^P \gamma_i (\Delta f_T)^i} \tag{4}$$

Wherein, $H_C$, $\beta_i (i=0 \ldots M)$, and $\gamma_i (i=0 \ldots P)$ are calibration coefficients, and the calibration coefficients are calibrated through curve fitting or solving vector equations via iterative method in the factory. The process can be divided into two steps:

Firstly, the frequency difference $\Delta f_H$ between humidity measuring resonator 103 and reference resonator 102 is measured under preset humidity $H_0 \ldots H_{(M+1)}$ and ambient temperature $T_0$, then the following equation can be established and $H_C$, $\beta_i (i=0 \ldots M)$ can be iteratively solved $$\begin{bmatrix} H_C^2 \\ (H_1 - H_0 - H_C)^2 \\ \vdots \\ (H_{M+1} - H_0 - H_C)^2 \end{bmatrix} - \begin{bmatrix} 1 & \Delta f_{H_0} & \ldots & (\Delta f_{H_0})^M \\ 1 & \Delta f_{H_1} & \ldots & (\Delta f_{H_1})^M \\ \vdots & \vdots & & \vdots \\ 1 & \Delta f_{H_{(M+1)}} & \ldots & (\Delta f_{H_{(M+1)}})^M \end{bmatrix} \begin{bmatrix} \beta_0 \\ \beta_1 \\ \vdots \\ \beta_M \end{bmatrix} = 0 \tag{5}$$

Then, the frequency difference $\Delta f_H$ between humidity measuring resonator 103 and reference resonator 102 as well as the frequency difference $\Delta f_T$ between reference resonator 102 and temperature measuring resonator 101 are measured based on the preset temperature $T_0 \ldots T_P$ and ambient humidity $H_0$, establishing the following equation and solve $$\gamma_i(i=0 \ldots P): \begin{bmatrix} H_C^2 \\ H_C^2 \\ \vdots \\ H_C^2 \end{bmatrix} - \begin{bmatrix} 1 & \Delta f_{H_0} & \ldots & (\Delta f_{H_0})^M \\ 1 & \Delta f_{H_0} & \ldots & (\Delta f_{H_0})^M \\ \vdots & \vdots & & \vdots \\ 1 & \Delta f_{H_0} & \ldots & (\Delta f_{H_0})^M \end{bmatrix} \quad (6)$$

$$\begin{bmatrix} \beta_0 \\ \beta_1 \\ \vdots \\ \beta_M \end{bmatrix} - \begin{bmatrix} 1 & \Delta f_{T_0} & \ldots & (\Delta f_{T_0})^P \\ 1 & \Delta f_{T_1} & \ldots & (\Delta f_{T_1})^P \\ \vdots & \vdots & & \vdots \\ 1 & \Delta f_{T_P} & \ldots & (\Delta f_{T_P})^P \end{bmatrix} \begin{bmatrix} \gamma_0 \\ \gamma_1 \\ \vdots \\ \gamma_P \end{bmatrix} = 0$$

Further, a larger number of measurement sampling points than the length of the undetermined vector (i.e. more than M+2 humidity sample points or more than P+1 temperature sample points) may be taken so as to be fitted to obtain the calibration parameters described above. Humidity measurement process and calibration methods described above enable the sensor to extract humidity directly. It should be noted that during the above humidity measurement, frequency drift caused by aging of devices has been compensated by frequency difference $\Delta f_T$ and $\Delta f_H$, thereby there is no need to re-calibrate the coefficients when used, thus ensuring the long-term stability of humidity measurement. Temperature change $\Delta T$ with respect to calibrated ambient temperature in the factory can be extracted via high order polynomial of $\Delta f_T$:

$$\Delta T - T_C = \sqrt[4]{\sum_{i=0}^{N} \alpha_i (\Delta f_T)^i} \quad (7)$$

Wherein, calibration coefficients $T_c$, $\alpha_i$ (i=0 ... N) are calibrated through solving vector equations via iterative method in the factory, comprising the following step: measuring the frequency difference between the reference resonator 102 and the temperature measuring resonator 101 based on the preset temperature $T_0 \ldots T_{N+1}$, establishing the following equation and solving $T_C$, $\alpha_i$(i=0 ... N) via iterative method:

$$\begin{bmatrix} T_C^2 \\ (T_1 - T_0 - T_C)^2 \\ \vdots \\ (T_{N+1} - T_0 - T_C)^2 \end{bmatrix} - \begin{bmatrix} 1 & \Delta f_{T_0} & \ldots & (\Delta f_{T_0})^N \\ 1 & \Delta f_{T_1} & \ldots & (\Delta f_{T_1})^N \\ \vdots & \vdots & & \vdots \\ 1 & \Delta f_{T_{(N+1)}} & \ldots & (\Delta f_{T_{(N+1)}})^N \end{bmatrix} \begin{bmatrix} \alpha_0 \\ \alpha_1 \\ \vdots \\ \alpha_N \end{bmatrix} = 0 \quad (8)$$

Similarly, in the above temperature measurement, frequency drift caused by aging of devices has been compensated by the frequency difference $\Delta f_T$, thereby there is no need to re-calibrate the coefficients when used, thus ensuring the long-term stability of humidity measurement.

In another embodiment of the present invention, said temperature and humidity sensor (not shown) collaborates with a remote sensing device to constitute a sensor system, wherein the remote sensing device can be an appropriate one known in the art and will not be elaborated here. Said remote sensing device employs band-limited frequency modulated continuous electromagnetic wave to illuminate and interrogate said sensor. After the sensor antenna receives the wave, the SAW resonators (including the temperature measuring resonator 101, the reference resonator 102 and the humidity measuring resonator 103) are motivated. At this time, the piezoelectric film substrate deforms and is charged, thereby it remains transient oscillations and feeds frequencies of resonators back to the remote sensing device via antennas after the irradiation is stopped. Said remote sensing device may include a human-machine interface and have the function of data processing, thereby it is able to directly display the temperature and humidity values locally and to alarm according to the preset threshold. Moreover, the remote sensing device may also include a wired or wireless repeater or hub, so as to achieve cluster and maintain simplex or duplex communications with a remote monitoring device, thereby deliver the temperature and/or humidity data to the remote control device to perform the cluster network networking capability.

Further, it should be noted that, when only temperature is to be measured, the sensor system of the present invention may not include a humidity measuring resonator. Similarly, when only humidity is to be measured, the sensor system of the present invention may not include a temperature measuring resonator. Moreover, depending on the application, more temperature measuring resonators and/or more humidity measuring resonator and/or more reference resonators may be provided in one sensor so as to improve accuracy and reliability of measurement.

Preferred embodiments of the present invention has been described in detail, while it is to be understood that, after reading the above teachings of the present invention, those skilled in the art may make various modifications to the present invention. All these equivalent forms also fall into the scope limited by attached claims of the present application.

What is claimed is:

1. A wireless temperature and humidity sensor, comprising a substrate, a feeding network, an antenna and surface acoustic wave resonators, wherein
   said surface acoustic wave resonators are fed by said feeding network through said antenna;
   said surface acoustic wave resonators comprise a reference resonator and a measuring resonator;
   said reference resonator and said measuring resonator have different rotation angles relative to the substrate's crystal orientation;
   the resonant frequency difference between said reference resonator and said measuring resonator is used to modulate the temperature and/or humidity to be measured; and
   said measuring resonator comprises a humidity measuring resonator and a temperature measuring resonator, said reference resonator has a different angle relative to the substrate's crystal orientation as compared to said humidity measuring resonator and said temperature measuring resonator, and the angle ranges from 25° to 45°.

2. The wireless temperature and humidity sensor according to claim 1, wherein
   said reference resonator, said humidity measuring resonator and said temperature measuring resonator are connected in parallel;
   said temperature measuring resonator has a different frequency-temperature coefficient from that of said reference resonator; and
   a hydrophilic coating is applied on the surface of said humidity measuring resonator such that said humidity measuring resonator has a different frequency-humidity coefficient from that of said reference resonator.

3. The wireless temperature and humidity sensor according to claim 1, wherein the sensor is able to monitor both temperature and humidity simultaneously, or to monitor temperature or humidity selectively.

4. The wireless temperature and humidity sensor according to claim 1, wherein said reference resonator and said measuring resonator are made on single or separate pieces of piezoelectric substrates with single layer or stratified layers.

5. The wireless temperature and humidity sensor according to claim 1, wherein said reference resonator and said measuring resonator are connected in parallel.

6. The wireless temperature and humidity sensor according to claim 2, wherein said temperature measuring resonator is placed within a closed packaging structure, so as to selectively monitor temperature.

7. The wireless temperature and humidity sensor according to claim 2, wherein said humidity resonator is packaged by a hydrophilic thin-film coating, so as to selectively monitor humidity.

8. The wireless temperature and humidity sensor according to claim 7, wherein said film coating is applied on the surface of said substrate and said humidity measuring resonator by vapor or liquid phase deposition.

9. The wireless temperature and humidity sensor according to claim 1, the wireless temperature and humidity sensor and a remote sensing device form a wireless temperature and humidity sensor system, wherein said remote sensing device scans the resonant frequency or the phase of the backscattering signal from said surface acoustic wave resonators and calculates the difference values therebetween, so as to extract temperature or humidity to be measured.

10. The wireless temperature and humidity sensor according to claim 9, wherein said temperature and humidity sensor operates at a frequency range different from that of adjacent sensors of same type, so as to facilitate simultaneously query by said remote sensing device.

11. The wireless temperature and humidity sensor according to claim 9, wherein said remote sensing device includes a human-machine interface to provide temperature and/or humidity readings, and a processing means to provide an alarm signal of preset threshold.

12. The wireless temperature and humidity sensor according to claim 9, wherein said remote sensing device comprises a wired or wireless repeater or hub, so as to achieve cluster and maintain simplex or duplex communications with a remote monitoring device.

13. The wireless temperature and humidity sensor according to claim 1, wherein said temperature measuring resonator is positioned adjacent to said humidity measuring resonator, a propagation direction of surface waves in said temperature measuring resonator and a propagation direction of surface waves in said humidity measuring sensor being parallel with each other and not in a same line, and said reference resonator is positioned on one side of said temperature measuring resonator and said humidity measuring resonator along the propagation direction of surface waves in said temperature measuring resonator and in said humidity measuring sensor.

14. A method for measuring temperature and/or humidity, wherein the wireless temperature and humidity sensor according to claim 1 is employed in the method, and the frequency difference between said reference resonator and said measuring resonator is used to modulate temperature and/or humidity.

15. The method for measuring temperature and/or humidity according to claim 14, further comprises the following steps:

arranging said wireless temperature and humidity sensor according to claim 1 on an object to be measured;

obtaining frequencies of said reference resonator and said measuring resonator and calculating the frequency difference between said reference resonator and said measuring resonator; and calculating the temperature and/or humidity of the object based on said frequency difference.

\* \* \* \* \*